United States Patent [19]

Lloyd

[11] 3,968,164
[45] July 6, 1976

[54] PROCESS FOR THE PRODUCTION OF ACROLEIN
[75] Inventor: John Edward Lloyd, Norton-on-Tees, England
[73] Assignee: Imperial Chemical Industries Limited, London, England
[22] Filed: Apr. 9, 1971
[21] Appl. No.: 132,885

Related U.S. Application Data
[62] Division of Ser. No. 625,948, March 27, 1967, Pat. No. 3,574,717.

[30] Foreign Application Priority Data
Apr. 7, 1966 United Kingdom............... 15653/66

[52] U.S. Cl............................ 260/604 R; 260/598; 260/599
[51] Int. Cl.$^2$........................................ C07C 45/04
[58] Field of Search............. 260/604 AC, 598, 599, 260/604 R

[56] References Cited
UNITED STATES PATENTS
3,446,825   5/1969   Schultz............................... 260/598
3,546,278   12/1970  Hayden et al................ 260/604 AC FOREIGN PATENTS OR APPLICATIONS
1,101,056   1/1868   United Kingdom.......... 260/604 AC
987,278     3/1965   United Kingdom.......... 260/604 AC OTHER PUBLICATIONS
Schullz, R. G., Tetrahedron, vol. 20, pp. 2809–2813, 1964.

Primary Examiner—Raymond V. Rush
Assistant Examiner—D. B. Springer
Attorney, Agent, or Firm—Cushman, Darby & Cushman

[57] ABSTRACT

Allene and substituted allenes react with certain specified nucleophiles including carboxylic acids, alcohols, water and hydrogen cyanide in the presence of a Group VIII noble metal salt catalyst, e.g., palladous acetate to give allyl and isopropenyl derivatives. The reaction may be carried out in the presence of a redox system as a copper salt which may optionally be regenerated by means of molecular oxygen.

1 Claim, No Drawings

PROCESS FOR THE PRODUCTION OF ACROLEIN

This is a division of our copending application, Ser. No. 625,948, filed Mar. 27, 1967, now U.S. Pat. No. 3,574,717, issued Apr. 13, 1971.

The present invention relates to the production of unsaturated organic compounds.

According to the invention unsaturated organic compounds are produced by a process which comprises reacting a compound of formula HX with an allene compound of formula

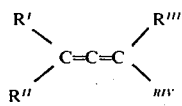

in the presence of a salt or complex of a noble metal of Group VIII of the Periodic Table, in which:

X is a nucleophilic element or group as hereinafter defined and $R^I$, $R^{II}$, $R^{III}$ and $R^{IV}$ which may be the same or different are organic or inorganic substituent groups.

In the formula HX X may be organic or inorganic in nature. The inorganic forms of HX are water HOH, ammonia $HNH_2$, and hydrogen cyanide HCN. The organic forms of HX are monohydric, dihydric and polyhydric alcohols and phenols, carboxylic acids, mercaptans and primary and secondary amines. Examples of suitable phenols are phenol itself, cresols and xylenols. Aliphatic alcohols containing 1 to 20 carbon atoms are very suitable, particularly aliphatic and cycloaliphatic alcohols containing 1 to 13 carbon atoms, for example methanol, isobutanol, cyclohexanol, ethylene and propylene glycols, glycerol and alcohols containing 8 to 13 carbon atoms made by the "OXO" process. Preferred organic forms of HX are the carboxylic acids, both aliphatic and aromatic. Benzoic acid and the phthalic acids, particularly terephthalic acid are examples of suitable aromatic acids. Aliphatic carboxylic acids containing 1 to 20 carbon atoms are particularly useful forms of HX, aliphatic carboxylic acids containing 1 to 6 carbon atoms, especially acetic acid, being preferred. Mono- and dimethylamine and mono- and di-ethylamine are examples of suitable amines for use in the process.

When HX is a carboxylic acid it has been found advantageous to incorporate an alkali metal or alkaline earth metal carboxylate in the process. Suitably sodium or lithium carboxylates may be used; for example when HX is acetic acid, lithium or sodium acetate may advantageously be incorporated in the reaction mixture. The concentration of the alkali metal or alkaline earth metal carboxylate is preferably in the range 0.1 to 2 molar.

The nature of the groups $R^I$, $R^{II}$, $R^{III}$ and $R^{IV}$ is not important as the process is essentially the reaction of the group >C=C=C<. $R^I$, $R^{II}$, $R^{III}$ and $R^{IV}$ can therefore represent a wide variety of substituent groups provided that they do not unduly influence the nature of the group >C=C=C< and are not of such a size as to sterically hinder the reaction of the group.

$R^I$, $R^{II}$, $R^{III}$ and $R^{IV}$ are suitably aliphatic, cycloaliphatic or aromatic groups or hydrogen. Preferred aliphatic and cycloaliphatic groups are alkyl groups containing 1 to 12 carbon atoms, particularly 1 to 6 carbon atoms, for example methyl and isobutyl groups. Cyclohexyl is a preferred cycloaliphatic group. Aromatic groups which may be used include phenyl, tolyl and benzyl groups. Although $R^I$, $R^{II}$, $R^{III}$ and $R^{IV}$ may contain olefinic unsaturation the product of the process when such substituent groups are present may comprise an increased number of compounds due to reaction of HX with the olefinic bond.

Suitable allene compounds for use in the process include allene itself, tetramethyl allene, monophenylallene, 1,1 dimethyl allene, 1,3 dimethylallene, trimethylallene, and the ethyl, n-propyl, isopropyl, n-butyl and isobutylallenes.

It is preferred to maintain a low concentration of the compound of formula

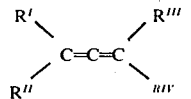

in the reaction solution, for exaple up to 10% by weight. This may be achieved by adding the compound continuously during the reaction. Where the compound of formula

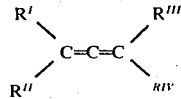

is gaseous under the reaction conditions, e.g. allene, it may conveniently be added continuously admixed with an inert gas such as nitrogen. In this case the partial pressure of the compound is preferably 5–30% of the total pressure.

The noble metals of Group VIII of the Periodic Table are ruthenium, rhodium, palladium, oamium, iridium and platinum. Of these palladium is preferred for use in the process.

Suitable salts of the noble metals are carboxylates, for example an acetate such as palladous acetate, and nitrates for example palladous nitrate. The salt may be in solution in the reaction medium or may be supported on an inert support such as alumina. The noble metal of Group VIII may form part of a complex. Suitable complexes are those comprising a metal salt complexed with one or more neutral ligands. Such ligands include phosphines such as triphenyl phosphine, phosphates such as triphenyl phosphate, phosphites such as triphenyl phosphite, and nitriles such as acetonitrile and benzonitrile. A particularly effective complex is the complex derived from a palladium salt such as palladous acetate or nitrate and benzonitrile. such complexes may be formed separately or in situ.

The salt or complex of the Group VIII metal may be used at a concentration in the range 0.001 to 2.0 molar, preferably in the range 0.01 to 0.1 molar.

The course of the reaction is as follows:

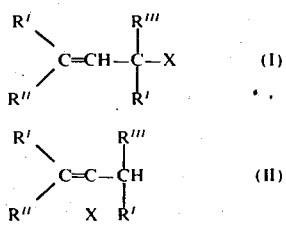

-continued

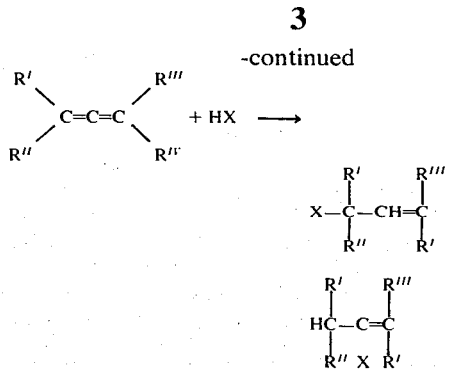

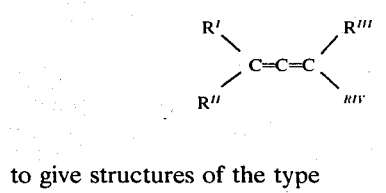

Additionally any one of I, II, III or IV may react with a molecule of

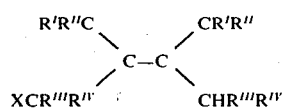

to give structures of the type

When HX is a carboxylic acid surprisingly high proportions of I and III, the allyl derivatives, are obtained. Thus when allene is reacted with acetic acid (X = acetate) at least three times as much allyl acetate (I) may be produced as isopropenyl acetate (II) and even higher to the extent that the isopropenyl acetate may even be present in only trace amounts.

The process may be carried out at temperatures in the range 20° to 180°C, preferably in the range 80° to 130°C.

Although the process is usually carried out at atmospheric pressure, elevated pressures may be used, particularly when one or other of the reactants is a gas under the reaction conditions. Suitable pressures are up to 10 atmospheres.

The process may be carried out in the liquid phase in an excess of the compound of formula HX or a solvent may be used. When the compound HX is an alcohol or carboxylic acid such as acetic acid, excess alcohol or acid may be used as solvent.

Solvents which may be used in the liquid phase form of the process include aliphatic hydrocarbons, for example pentane, hexane, octane or cyclohexane, aromatic hydrocarbons for example benzene, toluene or xylene, ethers for example diethyl ether, esters, for example dinonyl phthalate, and other well known solvents such as tetrahydrofuran, dioxane, dimethylacetamide, sulpholane, dimethyl sulphoxide, diglyme and benzonitrile. It will be noted that this list of inert solvents include compounds, e.g. benzonitrile, capable of complexing with the noble metal. Such compounds are very effective solvents for use in the process.

The process may also be carried out in the vapor phase by passing the compound of formulas HX, e.g. acetic acid, and compound of formula

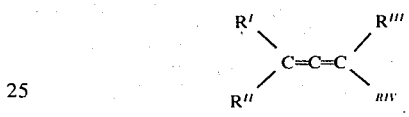

e.g. allene, over the catalyst deposited on an inert support such as alumina.

A modification of the process comprises incorporating in the reaction a redox system, which prevents precipitation of the noble metal, particularly palladium, by reductive side reactions. Metal salts are preferred redox systems, particularly copper or iron salts, for example copper carboxylates such as copper acetate, copper nitrate, iron carboxylates and iron nitrate. Reduction of the noble metal to metallic form is prevented by the existing property of the redox system which is itself converted to its reduced form. The use of a redox system is particularly advantageous when HX is water and is allene, as the first formed allyl alcohol, $HO-CH_2-CH=CH_2$, is oxidised under the reaction conditions to aerolein $O=CH-CH=CH_2$ a most valuable product. In this oxidation the noble metal (palladium is particularly suitable) is reduced but may be re-oxidised and retained in solution by the redox system.

The reduced form of the redox system may be re-oxidised by providing molecular oxygen in the process, the regeneration of the redox system being carried out either in situ or in separate reaction stage. As water is formed in the regeneration of the redox, and as water can be a reactant in the process, it is important that the need to regenerate the redox system should be kept to a minimum. A minor amount of water may be tolerated however, for example up to 5% by weight of the reaction medium.

The products of the process are of use as polymerisable monomers and chemical intermediates.

The invention will now be further described with reference to the following examples:

EXAMPLE 1

Allene was passed into a solution comprising 0.6 gram palladous acetate, 1 ml. benzonitrile and 5 mls. acetic acid for 24 hours at a temperature between 25° and 90°C. 200 to 225 mls. of allene were absorbed.

The proportion of allyl acetate to isopropenyl acetate in the solution at the end of the experiment was determined by vapour phase chromatographic analysis.

The ratio of allyl acetate to isopropenyl acetate was 4 to 1.

EXAMPLE 2

Allene was passed into a solution comprising 0.2764 gram of palladous acetate, 0.5 ml. of benzonitrile and 5 mls. of acetic acid for 5 hours at a temperature of 90°C. 500 mls. of allene were absorbed.

The amounts and proportion of allyl acetate and isopropenyl acetate in the solution remaning at the end of the experiment were again determined by vapour phase chromatography.

0.28 gram allyl acetate and 0.056 gram of isopropenyl acetate were detected.

Ratio of allyl acetate to isopropenyl acetate: 5 to 1

EXAMPLE 3

Allene was passed into a solution comprising 0.1343 gram of palladous acetate, 0.5 ml. of benzonitrile, 0.9786 gram of sodium acetate and 20 mls. of acetic acid for 3 hours at a temperature of 90°C. 580 mls. of allene were absorbed.

The products of the reaction in the amounts shown at the end of the experiment were as follows:

| | |
|---|---|
| allyl acetate | 0.25 gram |
| isopropyl acetate | 0.04 gram |
| 2-(acetoxy methyl)-5-methyl buta-1,5-dione | 1.2 gram |

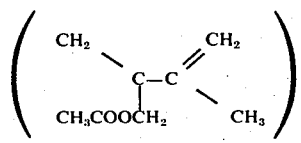

The yield of allyl acetate was 17 wt. %.

The ratio of allyl acetate to isopropehyl acetate was 6.25:1.

EXAMPLE 4

Allene was passed into a solution comprising 0.1238 gram of palladous acetate and 20 mls. acetic acid for 1½ hours at a temperature of 120°C. 285 mls. of allene were absorbed.

The products of the reaction and their amounts were determined by vapour phase chromatography. They were:

| | |
|---|---|
| allyl acetate | 0.04 gram |
| isopropanyl acetate | 0.05 gram |
| 2-(acetoxymethyl)-3-methyl buta-1,3-dione | 0.6 gram |

The yield of allyl acetate was 27 wt. %.

The ratio of allyl acetate to isopropenyl acetate was 4.8:1.

EXAMPLE 5

Allene was passed into a solution comprising 0.1244 grams of palladous acetate 0.1412 gram of triphenylphoaphine and 20 mls. acetic acid for 3½ hours at a temperature of 110°C. 500 mls. of allene were absorbed.

The reaction mixture was again analysed by vapour phase chromatography with the following results.

| | |
|---|---|
| allyl acetate | 0.1 gram |
| isopropenyl acetate | 0.04 gram |
| 2-(acetoxymethyl)-3-methyl buta-1,3-dione | 1.1 gram |

The yield of allyl acetate was 9.5 wt. %.

The ratio of allyl acetate to isopropenyl acetate was 3 to 1.

EXAMPLE 6

A mixture of 10% by volume allene in argon was passed into a solution comprising:

| | |
|---|---|
| palladous acetate | 0.28 gram |
| acetic acid | 20 mls. |
| benzonitrile | 0.1 ml. |

The temperature was 100°C., the pressure atmospheric, and the reaction time 5 hours. During this period approximately 150 mls. of allene were absorbed.

At the end of the reaction the yields of the products were estimated by vapour phase chromatography. These were

| | |
|---|---|
| 2-(acetoxymethyl)-3-methyl buta-1,3-dione | 0.15 gram |
| isopropenyl acetate | 0.006 gram |
| allyl acetate | 0.002 gram |

The yield of allyl acetate was 33 wt. %.

The ratio of allyl acetate to isopropenyl acetate was 15:1.

EXAMPLE 7

A mixture of 10% by volume allene in argon was passed into a solution comprising:

| | |
|---|---|
| palladous acetate | 0.2715 gram |
| acetic acid | 20 mls. |
| benzonitrile | 0.14 ml. |

The temperature was 85°C., the pressure atmospheric, and the reaction time 4½ hours.

At the end of the reaction the yields of the products were estimated by vapour phase chromatography. These were:

| | |
|---|---|
| 2-(acetoxymethyl)-3-methyl buta-1,3-dione | 0.12 gram |
| isopropenyl acetate | 0.008 gram |
| allyl acetate | 0.062 gram |

The yield of allyl acetate was 32.5 wt. %.

The ratio of allyl acetate to isopropenyl acetate was 8:1.

The results in Examples 6 and 7 demonstrate the advantages to be gained by maintaining a low allene concentration.

EXAMPLE 8

A solution comprising:

| | |
|---|---|
| acetic acid | 100 mls. |
| palladous acetate | 1.0148 gram |
| copper acetate monohydrate | 0.9914 gram | was refluxed (approximately 110°C.). Allene was bubbled slowly through the solution and samples were taken from the reaction vessel every few minutes. The allyl acetate concentration increased at a rate of 0.6 mol/liter/hour over the reaction period of 5½ hours.

At the end of the reaction the concentration of the products was estimated by nuclear magnetic resonance spectroscopy. The yields were:

| | |
|---|---|
| 2-(acetoxymethyl)-3-methylbuta-1,3-dione | 14.4 grams |
| allyl acetate | 32.7 grams |
| isopropenyl acetate | a trace. |

The yield of allyl acetate was 69.5 wt. %.

EXAMPLE 2

A solution comprising:

| | |
|---|---|
| acetic acid | 100 mls. |
| palladous acetate | 0.7142 gram |
| copper acetate monohydrate | 1.5144 gram | was refluxed (approximately 110°C.). Allene was bubbled slowly through the solution and the allyl acetate removed continuously as it was formed. After 5 hours reaction time the yield of products as determined by vapour phase chromatography was:

| | |
|---|---|
| 2-(acetoxymethyl)-3-methyl buta-1,3-dione | 1.8 gram |
| allyl acetate | 5.44 grams |
| isopropenyl acetate | a trace. |

The yield of allyl acetate was 75 wt. %.

Examples 8 and 9 demonstrate the beneficial effect of a copper salt on the reaction.

I claim:

1. A process for the production of acrolein which consists essentialy of reacting water with allene at a temperature of 20°C to 180°C and a pressure from atmospheric to 10 atmospheres in the liquid phase and in the presence of a catalytic amount of a palladium salt selected from the group consisting of palladium acetate, palladium nitrate and complexes thereof with benzonitrile and a copper or iron redox system selected from the group consisting of copper carboxylate, iron carboxylate, copper nitrate and iron nitrate whereby allyl alcohol is formed as an intermediate and oxidized in situ to acrolein, the liquid phase being excess water or inert organic solvent.

* * * * *